US008403846B1

(12) United States Patent
Cienfuegos

(10) Patent No.: US 8,403,846 B1
(45) Date of Patent: Mar. 26, 2013

(54) NETWORKED TRIAGE SYSTEM AND METHOD

(76) Inventor: Juan Enrique Cienfuegos, San Antonio, TX (US)

( * ) Notice: Subject to any disclaimer, the term of this patent is extended or adjusted under 35 U.S.C. 154(b) by 698 days.

(21) Appl. No.: 12/589,348

(22) Filed: Oct. 22, 2009

Related U.S. Application Data

(60) Continuation-in-part of application No. 11/998,951, filed on Dec. 3, 2007, now Pat. No. 7,674,227, which is a division of application No. 11/291,391, filed on Dec. 1, 2005, now Pat. No. 7,326,179.

(60) Provisional application No. 60/633,046, filed on Dec. 2, 2004.

(51) Int. Cl.
*A61B 5/00* (2006.01)

(52) U.S. Cl. .......................................................... 600/300

(58) Field of Classification Search .................. 600/300; 362/253, 231
See application file for complete search history.

(56) References Cited

U.S. PATENT DOCUMENTS

| | | | | |
|---|---|---|---|---|
| 5,793,882 | A | 8/1998 | Piatek et al. | |
| 6,198,394 | B1 | 3/2001 | Jacobsen et al. | |
| 6,305,605 | B1 | 10/2001 | Goetz et al. | |
| 6,499,658 | B2 | 12/2002 | Goetz et al. | |
| 6,761,312 | B2 | 7/2004 | Piatek et al. | |
| 7,596,608 | B2 | 9/2009 | Alexander et al. | |
| 7,629,881 | B2 * | 12/2009 | Gao et al. | 340/539.13 |
| 2008/0228045 | A1 | 9/2008 | Gao et al. | |
| 2009/0018875 | A1 | 1/2009 | Monatesti | |
| 2009/0069642 | A1 | 3/2009 | Gao et al. | |

* cited by examiner

*Primary Examiner* — Anable Ton
(74) *Attorney, Agent, or Firm* — Rafael V. Baca; Baca Law Firm, PLLC

(57) ABSTRACT

A networked triage system for prioritizing medical care administered to an injured user including a networked monitoring system and a plurality of user groups. Each group includes a portable network interface and a plurality of illuminated display systems. Each illuminated display system couples to an injured user and includes a plurality of light emitters. Each light emitter provides a predetermined wavelength of light than the other light emitters from the plurality of light emitters. Operatively, each respective predetermined wavelength provides information relating to a corresponding predetermined status of the user. Each illuminated display system includes an id tag processor that facilitates emission of identification signals for receipt by the portable network interface. Based on the identification signal, the portable network interface generates a network signal for receipt by the networked monitoring system. The network monitoring system can assess the degree of injury of several user groups in a triage situation.

20 Claims, 11 Drawing Sheets

FIG. 5A
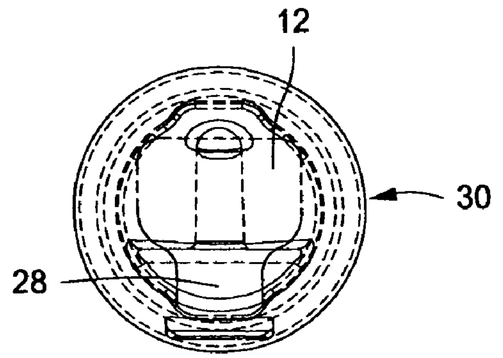
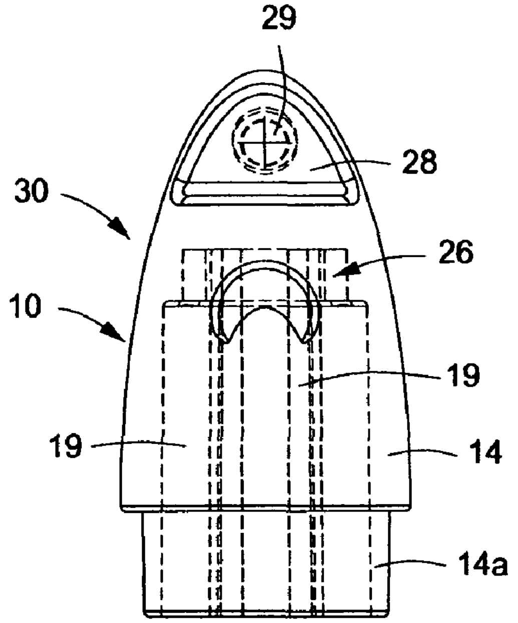
FIG. 5B
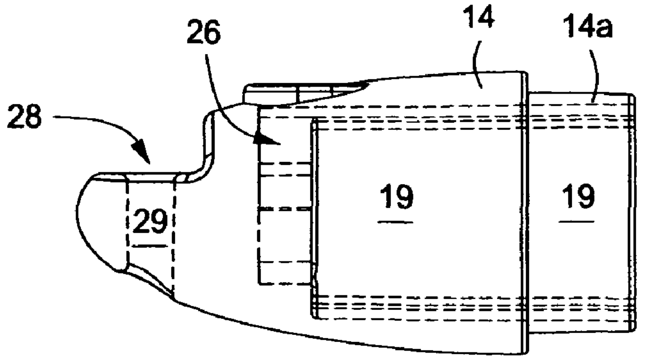
FIG. 5C

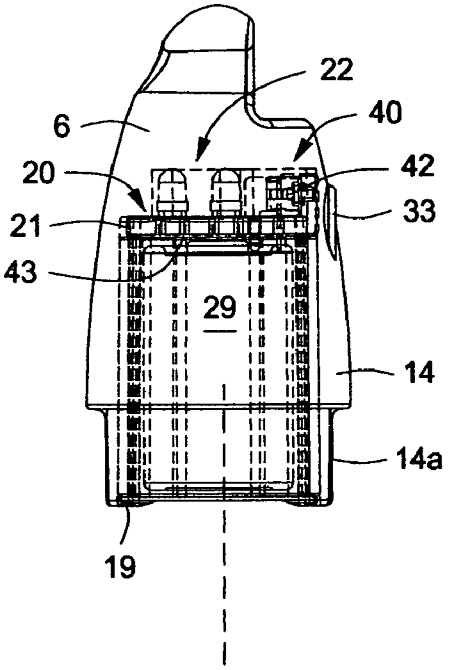
FIG. 7A
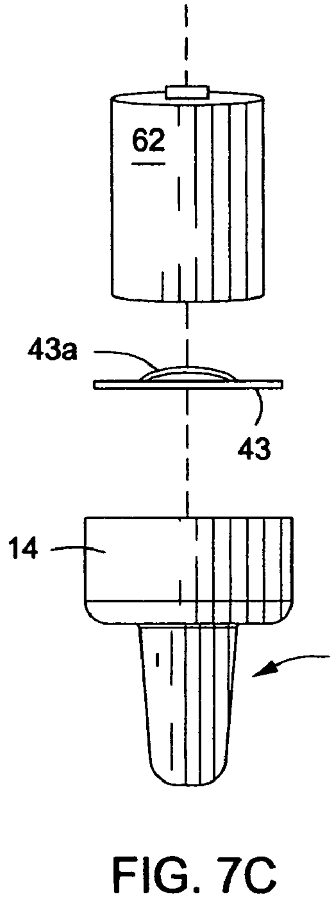
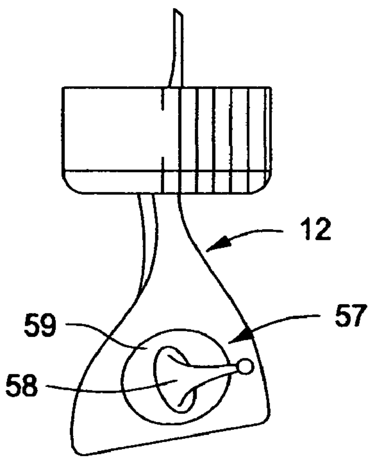
FIG. 7C
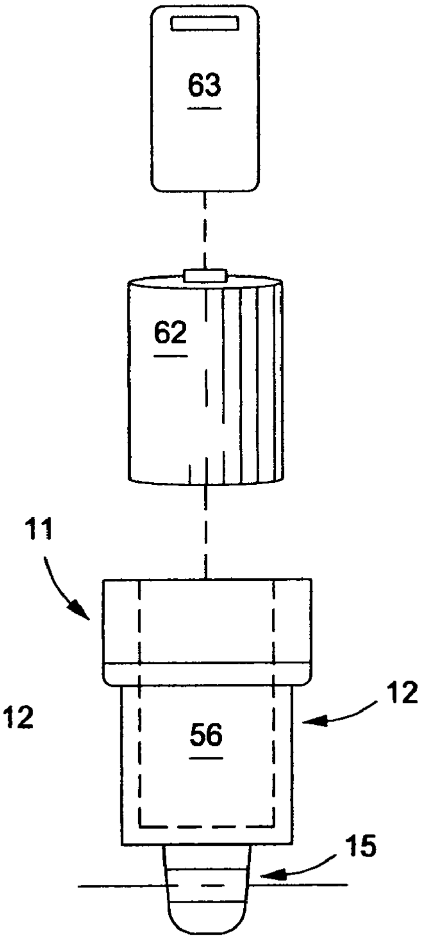
FIG. 7B
FIG. 7D

NETWORKED TRIAGE SYSTEM AND METHOD

CROSS REFERENCE TO RELATED APPLICATIONS

This application is a Continuation-in-Part of a Divisional application Ser. No. 11/998,951 filed Dec. 3, 2007, now U.S. Pat. No. 7,674,227 of Non-Provisional application Ser. No. 11/291,391, filed Dec. 1, 2005, which claims benefit under 35 U.S.C. §119(e) from prior U.S. Provisional Patent Application Ser. No. 60/633,046 filed on Dec. 2, 2004 entitled "An Illuminated Display System and Method of Use", by inventor Juan Enrique Cienfuegos, the entirety of disclosures of the above referenced Applications is hereby incorporated by reference as if fully set forth herein.

BACKGROUND OF THE INVENTION

1. Field of the Invention

The present invention generally relates to a networked triage system for placement on a user or receiving object. More particularly, but not by way of limitation, the present invention relates to a networked triage system and method for visually displaying information from a selection of light signals with programmable illuminated display systems whereby the information, for example, may be used for prioritizing the degree of medical care administered to a user.

2. Description of the Related Art

In the past, the concept of assessing an individual's medical condition and prioritizing that individual's need for medical care with respect to others requiring assistance is a concept commonly known as "Triage". Triage is one of the first applications of medical care applied to an individual and is often used as a technique to address the most seriously injured first. The triage concept is applied to humans and animals alike and in a variety of patient care settings including hospital emergency rooms, in the field with emergency medical service providers such as with natural disaster conditions and in battlefield settings. Illustratively, the triage concept is applied by the military, homeland security, and the federal emergency management agency (FEMA).

Generally, triage techniques attempt to sort patients into categories for transport and immediate medical treatment. Triage is administered oftentimes in imperfect conditions where immediate medical care is limited, time is critical, and patients are prone to inaccurately advocating their precise medical condition.

Triage assessors generally tag patients according to the degree of injury. Many typical examples of triage tags are based on color coded information cards by which an assessor provides a written description of the patient's condition on that paper card.

Illustratively, in a battlefield setting, either a combat medic or corpsman provides triage assessments to injured soldiers on the battlefield. In practice, a medic is personally at risk from being fired on or the hazardous conditions associated with the battlefield. A medic's triage assessment must not only be accurate, but must be quickly provided so as not jeopardize the health of the injured soldier or of the medic themselves. Many times, a medic is not given the opportunity to provide a written description or even color code an injured soldier accordingly. Furthermore, battlefield conditions hinder one's ability to accurately read a corresponding triage card. Illustratively, smoke, dust, and changing weather conditions obscure one's ability to determine the triage status of an injured solider at a distance. Moreover, conditions such as complete darkness, underwater settings or in buried conditions could render the determination of written information on one's triage card as improbable. These difficulties are amplified when caring for several injured soldiers at the same time without a unified way to remotely prioritize injury. Unfortunately, there is no known device or method for quickly and accurately providing triage status at a distance, such as status of an injured soldier in various battlefield settings.

Therefore, a need exists for a system and method for placement on a user that quickly and accurately provides information relating to the degree of injury of the user among at least one group of other users. There is also a need for a system and method for quickly and accurately providing information including triage information in varied visibility conditions and at a distance. Many other problems and disadvantages of the prior art will become apparent to one skilled in the art after comparing such prior art with the present invention as herein described.

SUMMARY OF THE INVENTION

Aspects of the invention are found in a networked triage system for prioritizing medical care administered to an injured user. In one aspect, the networked triage system includes a plurality of user groups and a networked monitoring system with each user group in communication with the networked monitoring system. Each group includes a portable network interface and a plurality of illuminated display systems. Each illuminated display system couples to an injured user and includes a plurality of light emitters. Each light emitter provides a predetermined wavelength of light than the other light emitters from the plurality of light emitters. In operation, each respective predetermined wavelength provides information relating to a corresponding predetermined status of the user.

In one aspect, each illuminated display includes an id tag processor that facilitates emission of identification signals for receipt by the portable network interface. Based on the identification signal, the portable network interface generates a network signal for receipt by the networked monitoring system.

In one aspect, the network signal includes information regarding the identification of each illuminated display system and the status of the corresponding illuminated light emitter from each illuminated display. In this manner, the network monitoring system can assess the degree of injury of several user groups in a triage situation.

In one aspect, the portable network interface reads and writes information with at least one memory device. The at least one memory device is used in medical triage in conjunction with an illuminated display system and stores identification signals and command signals associated with the desired illuminated display system. In one aspect, the at least one memory device is color coded based on a color scheme associated with medical triage.

In one aspect, an illuminated display system includes an interface module having a module processor, a memory unit, and at least one programming interface coupled to the module processor. The memory unit stores a lighting operation sequence that acts as the protocol for selecting a desired light emitter from the plurality of light emitters.

Operatively, at least one programming interface receives a command sequence that integrates with the lighting operation sequence to define a reprogrammed lighting operation sequence. Thus, each light emitter is selected from the plurality of light emitters according to a reprogrammed lighting operation sequence.

In one aspect, the module processor receives a voltage from the selector indicating the desired light emitter for illumination thereof and stores the corresponding last lit information in the memory unit. Upon reestablishment of power of the interface module, the last lit information is retrieved to illuminate the desired light emitter.

In one aspect, a method for organizing medical care is as follows. Operatively, a plurality of illuminated display systems are provided with each illuminated display system including an identification or "id" tag processor. An illuminated display system from the plurality of illuminated display systems is coupled to an injured user. The identification tag processor facilitates the generation of and emission of an identification signal. Each identification signal emitted from a respective illuminated display system of the plurality of illuminated display systems is received via a portable network interface. The portable network interface includes an electronic interface and receives a plurality of identification signals.

In one aspect, a predetermined color is assigned to each memory device of a plurality of memory devices. A clinical assessment is administered to the injured user and a triage status is assigned to the injured user based on a pre-determined degree of injury.

In one aspect, a memory device is selected that exhibits a color consistent with the triage status of the injured user. The memory device is coupled to the electronic interface. Specifically, in one exemplary embodiment, the electronic interface reads output and writes input electronically to the at least one memory device. The selected memory device is assigned to the injured user. Other aspects, advantages, and novel features of the present invention will become apparent from the detailed description of the present invention when considered in conjunction with the accompanying drawings.

BRIEF DESCRIPTION OF THE DRAWINGS

The present invention is illustrated by way of example and not by limitation in the accompanying figures, in which like references indicate similar elements, and in which:

FIG. 3 are orthographic views from the top illustrating one exemplary embodiment of an illuminated display system, in particular.

FIG. 4 are orthographic views illustrating one exemplary embodiment of an illuminated display system, in particular.

FIG. 5 are orthographic views illustrating one exemplary embodiment of an illuminated display system, in particular, FIG. 5*a* shows the illuminated display system from the back; FIG. 5*b* shows the illuminated display system illustrating a base body having an attachment flange; and FIG. 5*c* shows an illuminated display system having an alignment element;

FIG. 6 illustrate isometric views of an illuminated display system, in particular.

FIG. 7 are exploded orthographic views of an illuminated display system, in particular, FIG. 7*a* illustrates an interface module coupled with a chamber support for receiving a power source and an electronic identification tag, FIG. 7*b* illustrates an second portion including a sensor assembly, FIG. 7*c* illustrates a base body that forms an interference fit with an attachment flange, and FIG. 7*d* illustrates a second portion defining a storage chamber;

FIG. 8 generally illustrate various embodiments of the interface module, in particular.

FIG. 9 generally illustrate components for electrically coupling a power source to an interface module, in particular.

FIG. 10 generally illustrate a float appendage for engagement with an illuminated display system, in particular.

FIG. 11 generally illustrate a modifier unit for engagement with an illuminated display system, in particular.

Skilled artisans appreciate that elements in the Figures are illustrated for simplicity and clarity and have not necessarily been drawn to scale. For example, the dimensions of some of the elements in the Figures may be exaggerated relative to the other elements to help improve understanding of the embodiments of the present invention.

DETAILED DESCRIPTION

For a more complete understanding of the present invention, preferred embodiments of the present invention are illustrated in the Figures. Like numerals being used to refer to like and corresponding parts of the various accompanying drawings. It is to be understood that the disclosed embodiments are merely exemplary of the invention, which may be embodied in various forms.

FIGS. 1-9 and 12 generally illustrate one aspect, among others, of an illuminated display system 5 of a plurality of illuminated display systems 101 within a networked triage system 100. Each illuminated display system 5 is typically placed on a user or receiving object. Generally, an illuminated display system provides information associated with the user or receiving object through light emission at various wavelengths. In this application, the terms "user" and "receiving element" respectively refer to a living being and non-living object by which an illuminated display system is attached to. For example, an illuminated display system provides information relating to the injury of a user in a triage situation such as the degree of injury, the nature of injury, and likelihood of survival. Moreover, in this application, the term "light" refers to the entire electromagnetic spectrum of light including infrared light whereas the term "visible light" refers to a wavelength range of the electromagnetic spectrum that is observable to the human eye. Each respective predetermined wavelength of light provides information relating to a user's status, such as information relating to the degree of injury of the user in a triage setting.

Specifically as viewed in FIGS. 1-3, 4*a*, 7*a*, and 8, the illuminated display system 5 includes a plurality of light emitters 22. At least one light emitter from the plurality of light emitters 22 is selected for illumination thereof according to the injury of the user. The illuminated display system 5 may then be attached to the user or receiving object while operatively illuminated. Illumination of a desired light emitter provides information describing the current status of the user, such as, among others, the kind of injury received, the likelihood for injury recovery or the location of the injured party.

Figure 1:
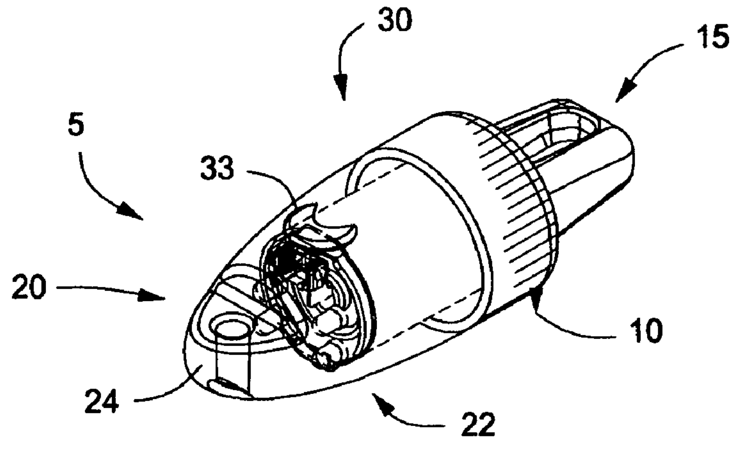
FIG. 1 is an isometric view from the top illustrating an illuminated display system for placement on an user according to the present invention, the illuminated display system includes a plurality of light emitters that individually emit a predetermined wavelength band relating to the user's status.

Referring to FIG. 1, the illuminated display system 5 includes a base assembly 10. The base assembly 10 includes a display interface 20. In one exemplary embodiment, the display interface 20 is coupled to the base assembly 10. As shown in FIG. 1, the plurality of light emitters 22 are incorporated with the display interface 20.

The illuminated display system 5 includes a dial assembly 30. The dial assembly 30 is operatively coupled to the base assembly 10.

The illuminated display system 5 further includes a selector 33. As shown in the embodiment of FIG. 1, the selector 33 is disposed on the dial assembly 30. Operatively, according to a lighting program sequence as discussed below, the selector 33 applies a voltage to a desired light emitter from the plurality of light emitters 22 for illumination thereof. Thus, according to a lighting program sequence the selector 33 either engages or disengages a desired light emitter from the plurality of light emitters. In one exemplary embodiment, the illuminated display system 5 is rendered in a consistent, electrically "off" position until the selector 33 engages with a light emitter from the plurality of light emitters 22. In this manner, the illuminated display system 5 will be illuminated as desired.

Moreover, in one exemplary embodiment, the dial assembly 30 further includes an interface module 40. Referring to FIGS. 7 and 8, the interface module 40 includes a module processor 65, a memory unit 64*a*, and at least one programming interface 67 coupled to the module processor 65. In one exemplary embodiment, the module processor 65 receives a voltage from the selector 33 indicating the desired light emitter for illumination thereof and stores corresponding last lit information in the memory unit 64*a*. Upon reestablishment of power to the interface module 40, the last lit information is retrieved from the memory unit 64*a* to re-illuminate the desired light emitter via the module processor 65. Accordingly, due to storage of last lit information in the memory unit 64*a*, triage status information of the injured user as indicated by the desired illuminated light emitter is maintained despite power loss to the illuminated display system 5.

Each light emitter from the plurality of light emitters 22 radiates a different wavelength of light than other light emitters from the plurality of light emitters 22. In this manner, each respective predetermined wavelength of light provides information associated with the status of a user or receiving object. For example, each light emitter provides correspondingly different information from the other emitters as related to the degree of injury of an injured user, such as a soldier. Those of ordinary skill in the art will readily recognize that each respective predetermined wavelength represents corresponding predetermined information to be conveyed about the user. Each light emitter is selected from the plurality of light emitters according to a lighting operation sequence stored in the memory unit 64*a*. Ultimately, as a desired light emitter is selectively illuminated, the illuminated display system 5 when placed on an injured user facilitates quick, efficient prioritization of the injured user for future treatment and transport in a triage setting.

In one exemplary embodiment, an illustrative lighting operation sequence among others is described as follows. After making a brief clinical assessment of an injured user, a light emitter exhibiting a distinct wavelength is illuminated to indicate the degree of injury according to a predetermined assignment of triage wavelength bands for illumination. With the illustrative lighting operation sequence, a selector is pressed once to access infrared light, and pressed twice to obtain blinking infrared light. The selector is pressed a third time for red light, a fourth time for green light, a fifth time for blue light, and a sixth time to end the lighting operation sequence. The lighting operation sequence may then be restarted in the manner described above. With another illustrative lighting operation sequence, a selector is pressed once to access red light, and pressed twice to obtain amber or yellow light. The selector is pressed a third time for green light, a fourth time for blue light, and a fifth time to end the lighting operation sequence. The lighting operation sequence may then be restarted in the manner described above. Those of ordinary skill in the art will readily recognize that the lighting operation sequence may include any combination of either continuous or intermittently illuminated light emissions at various wavelengths.

Figure 8B:
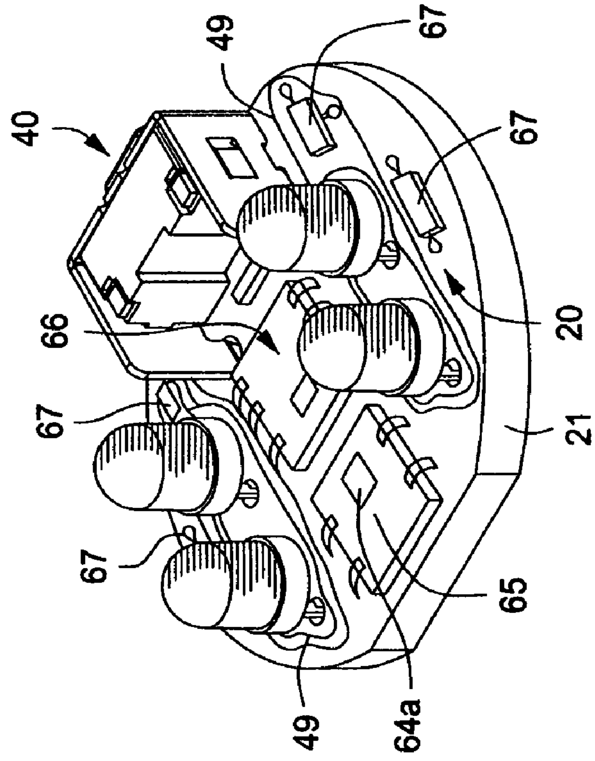
FIG. 8*b* illustrates an isometric view of an interface module including an id tag processor.
Figure 8A:
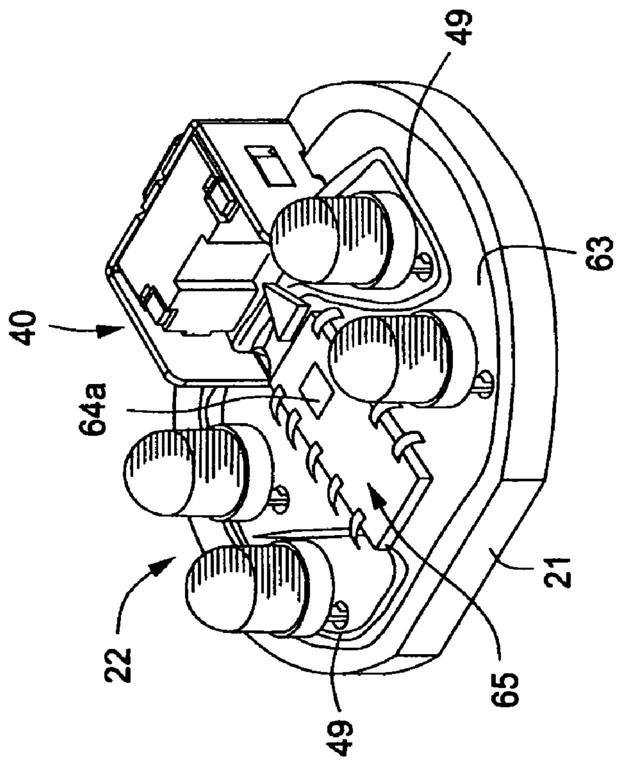
FIG. 8*a* illustrates an isometric view of an interface module including a module processor.
Figure 8C:
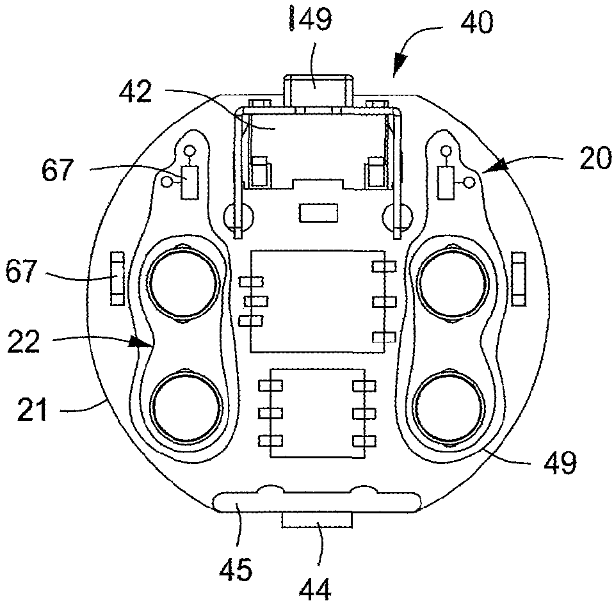
FIG. 8*c* illustrates an isometric view of an interface module including programming pads.
Figure 8D:
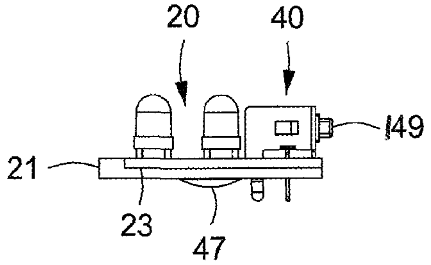
FIG. 8*d* is an orthographic view from the side of a display interface.
Figure 8E:
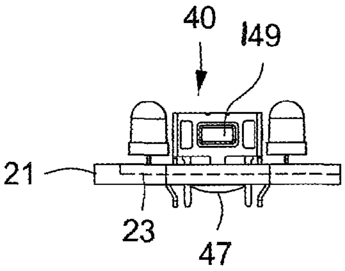
FIG. 8*e* is an orthographic view from the side illustrating a display interface.

In operation, as shown in FIGS. 8*c, d*, and *e*, as the selector 33 is pressed the interface module 40 receives a compressive force as applied to a mode activation interface 149. Accordingly, the physical input applied by the selector 33 on the mode activation interface 149 is converted to an electrical signal output by the selector unit 42 coupled to the mode activation interface 149. The resulting electrical signals are then received and manipulated by a module processor 65 provided by the interface module 40. Based on the lighting operation sequence, the module processor 65 facilitates the activation of a desired light emitter from the plurality of light emitters 22. In one exemplary embodiment, information associated with the activation of the desired light emitter is stored in a memory unit 64*a* coupled to the module processor 65.

In one exemplary embodiment, the plurality of light emitters 22 includes a light emitting diode for emitting light at various wavelengths along the entire electromagnetic spectrum. In particular, the plurality of light emitters 22 includes a light emitting diode for providing an infrared wavelength band of light. The plurality of light emitters 22 includes a light emitting diode for providing a wavelength band of white light. The plurality of light emitters 22 includes a light emitting diode for radiating a wavelength band of amber visible light. The plurality of light emitters 22 includes a light emitting diode for radiating a wavelength band of red visible light.

The plurality of light emitters 22 includes a light emitting diode for supplying a green wavelength band of visible light. The plurality of light emitters 22 further includes a light emitting diode for generating a blue wavelength band of visible light. The plurality of light emitters 22 includes a light emitting diode for supplying an ultraviolet wavelength band of visible light. In one exemplary embodiment, the plurality of light emitters 22 may include an single light emitting diode arranged on the display interface 20 for providing blue, green, and red visible light in addition to an infrared band and an intermittent band of infrared light.

Those of ordinary skill in the art will readily recognize other widely known light emitters for selective illumination about the display interface 20 that emit light at a wide band of various wavelengths. Illustratively, in one exemplary embodiment, the plurality of light emitters 22 includes inorganic light emitting diodes. In one exemplary embodiment, the plurality of light emitters 22 includes organic light emitting diodes. In one exemplary embodiment, the plurality of light emitters 22 includes a combination of inorganic and organic light emitting diodes. In one exemplary embodiment, the plurality of light emitters 22 may include an incandescent light emitter. In one exemplary embodiment, the plurality of light emitters 22 includes a plasma light emitter, such as, among others, a fluorescent light and a mercury vapor light. In one exemplary embodiment, the plurality of light emitters 22 may include electroluminescent light. In one exemplary embodiment, the plurality of light emitters 22 includes a LASER light. In one exemplary embodiment, the plurality of light emitters 22 includes a Liquid Crystal Display, LCD, light emitter.

In one exemplary embodiment, to amend in part or supersede the lighting operation sequence, the at least one programming interface 67 receives a command sequence. Illustratively, in one exemplary embodiment, the at least one programming interface 67 comprises a plurality of program pads for a peripheral interface controller processor that receive a command sequence from a programming device such as, among others, an In-Circuit Programmer and an In-Circuit Debugger (ICD). In this manner, a portable programming device can be taken anywhere to either amend or entirely supersede the lighting operation sequence.

On its receipt, the command sequence integrates with the lighting operation sequence via the module processor 65 to thus define a reprogrammed lighting sequence. In one exemplary embodiment, the reprogrammed lighting sequence is stored in memory via the module processor 65. As such, each light emitter is selected from the plurality of light emitters 22 according to the reprogrammed lighting operation sequence. In effect, the reprogrammed lighting operation sequence becomes the new lighting operation sequence for storage in the memory unit 64*a* and for future execution by the illuminated display system 5.

Shown in FIGS. 4-7, each illuminated display 5 for illustrative purposes is generally divided as the base assembly 10 positioned on one side of the interface module 40 and the dial assembly 30 positioned on another side of the interface module 40. As such, the base assembly 10 includes a base body 14 whereas the dial assembly 30 includes a display body 6. In one exemplary embodiment a combination of the base body 14 and the display body 6 may be composed of a transparent material. In one exemplary embodiment a combination of the base body 14 and the display body 6 may be composed of a translucent material. In one exemplary embodiment a combination of the base body 14 and the display body 6 may be composed of an opaque material. In one exemplary embodiment, a combination of the base body 14 and the display body 6 may be composed of a semi-resilient material, such as silicone. In one exemplary embodiment, a combination of the base body 14 and the display body 6 may be composed of a water proof material.

Figure 10A:
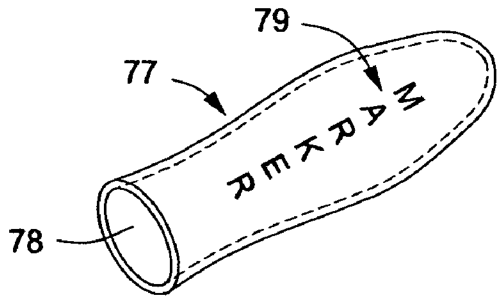
FIG. 10*a* is an isometric view showing one exemplary embodiment of a float appendage.
Figure 10B:
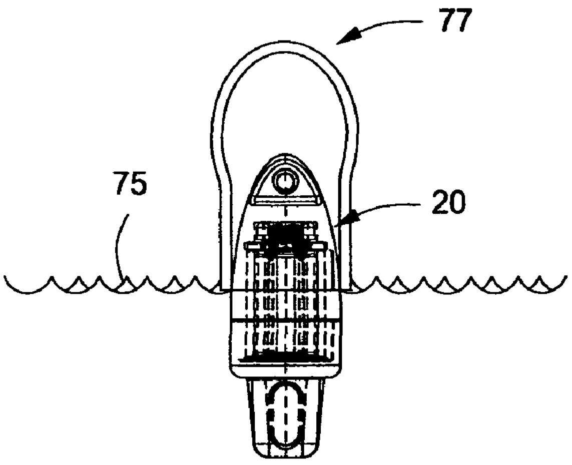
FIG. 10*b* is a schematic view illustrating a float appendage positioning a display interface above a water line.
Figure 10C:
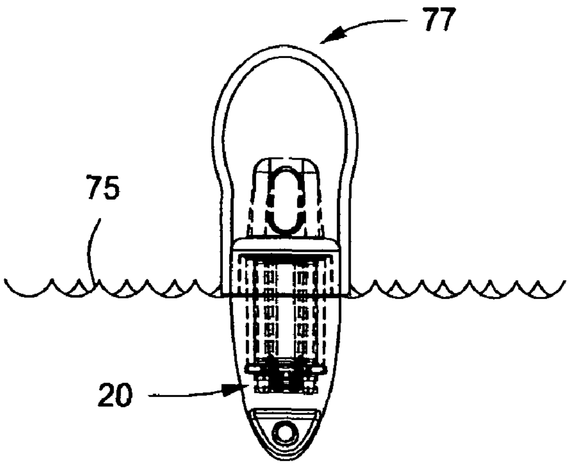
FIG. 10*c* is a schematic view illustrating a float appendage positioning a display interface below the water line.

Optionally, FIG. 10 generally shows a float appendage 77 that couples with an illuminated display system 5. The float appendage 77 is a thin, enveloped membrane defining an appendage opening 78. In general, the appendage opening 78 is fitted over the illuminated display system 5 with an interference fit that establishes a hermetic seal trapping a pocket of air within the float appendage 77 and the illuminated display system 5 that establishes the seal. In one exemplary embodiment, indicia 79 such as, among others, merchandising information and safety information may be disposed on the outer surface of the float appendage 77 as shown in FIG. 10*a*. Illustratively, FIG. 10*b* shows one exemplary embodiment of a float appendage 77 positioning a display interface 20 above a waterline 75 to observe illuminated light emitters from the display interface 20 from above the waterline 75. Similarly, FIG. 10*c* shows one exemplary embodiment of a float appendage 77 positioning a display interface 20 below a waterline 75 to observe illuminated light emitters from the display interface 20 from below the waterline 75.

Figure 2:
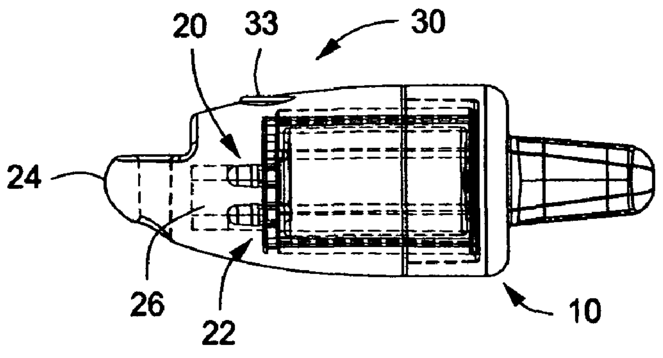
FIG. 2 is an orthographic view from the side illustrating one exemplary embodiment of an illuminated display system.
Figure 3A:
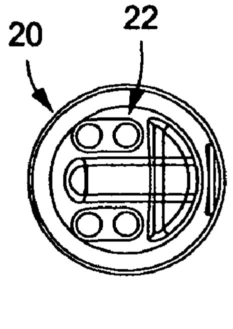
FIG. 3*a* is an orthographic view from the front illustrating a display interface of the illuminated display system.
Figure 3B:
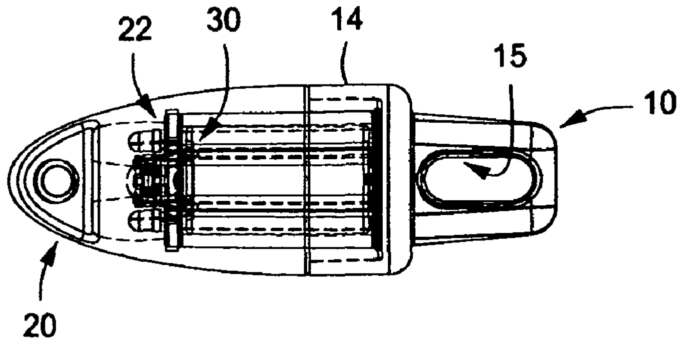
FIG. 3*b* is an orthographic view from the top illustrating an illuminated display system having a fastening interface.
Figure 4A:
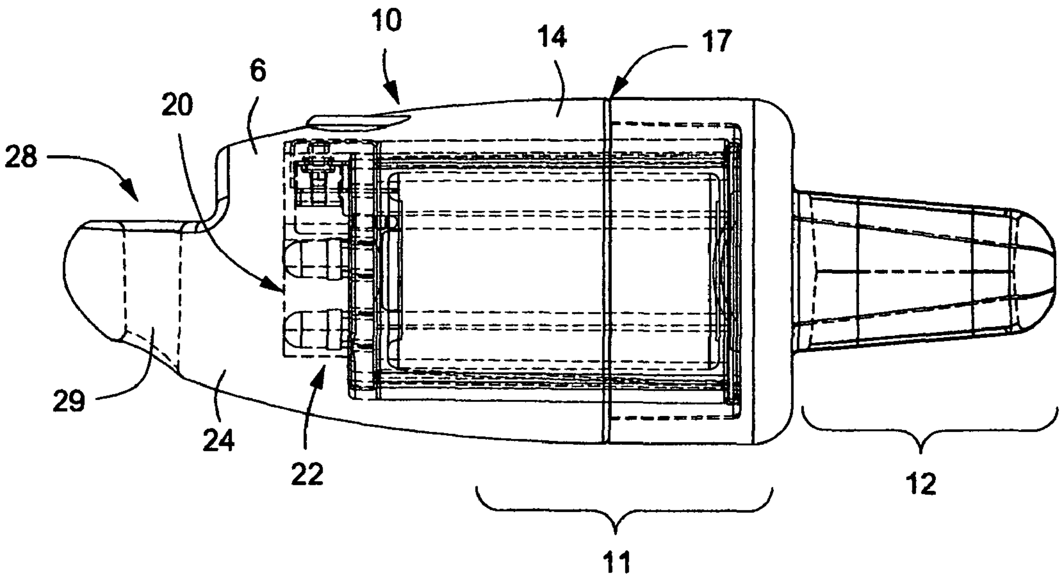
FIG. 4*a* shows an illuminated display system having a first portion and a second portion.
Figure 4B:
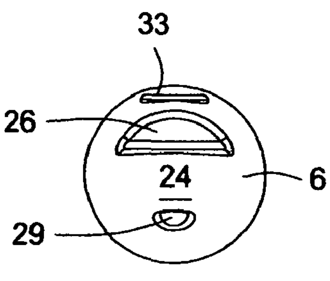
FIG. 4*b* shows an orthographic view from the front illustrating an optical modifier.
Figure 4C:
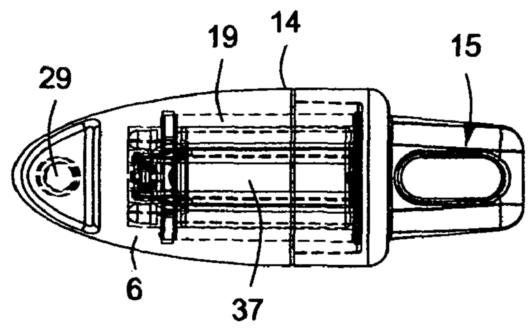
FIG. 4*c* shows an orthographic view from the top illustrating a power source positioned within a display system body.

Specifically referring to FIGS. 2, 4, and 7, the display body 6 includes an optical lens 24 for facilitating the transmission of light therethrough. Optionally, the dial assembly 30 includes optical modifiers 26. In one exemplary embodiment, as shown in FIG. 2, the display body 6 forms a series of chambers that define the optical modifiers 26. Operatively, the optical modifiers 26 facilitate the manipulation of light emission from the interface module 40 through the dial lens 24. In one exemplary embodiment, the optical modifiers 26 amplify light through the dial lens 24. In one exemplary embodiment, the optical modifiers 26 filter light through the dial lens 24. In one exemplary embodiment, the optical modifiers 26 diffuse light through the dial lens 24.

Figure 11A:
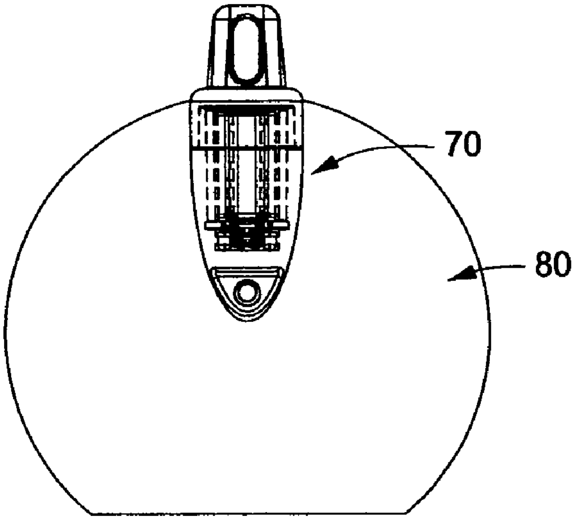
FIG. 11*a-c* show various exemplary configurations of a modifier unit.
Figure 11B:
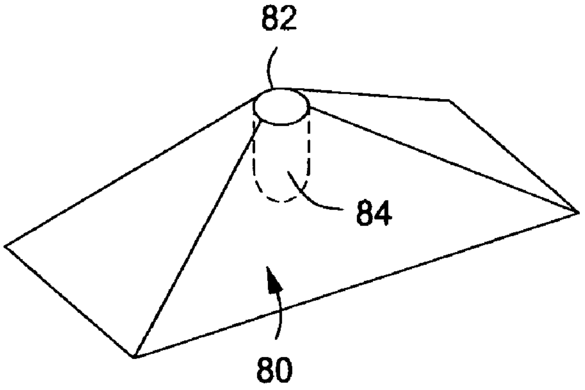
Figure 11C:
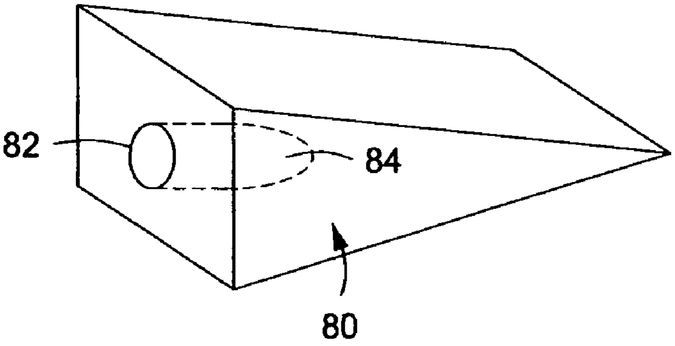

Optionally, FIG. 11 generally illustrates a modifier unit 80 for receiving the illuminated display system 5 therein. The modifier unit 80 facilitates manipulation of light emission from the illuminated display system 5. In one exemplary embodiment, the modifier unit 90 amplifies light emission from the illuminated display system 5. Furthermore, the modifier 80 supports the illuminated display system 5 during long periods. FIGS. 11*a*-*c* shows various exemplary configurations of a modifier unit 80.

Figure 6C:
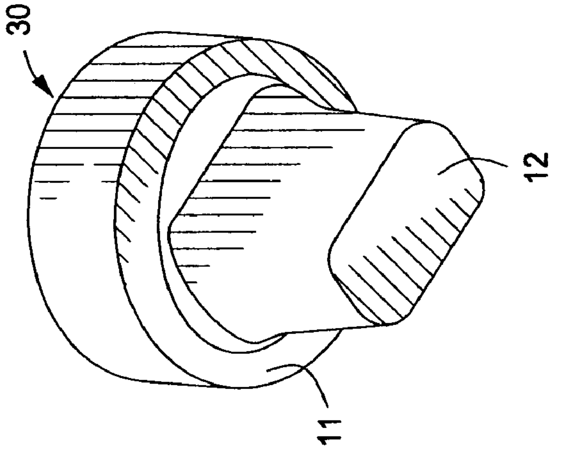
FIG. 6*c* is an orthographic view illustrating one exemplary embodiment of a second portion of a base body.
Figure 6B:
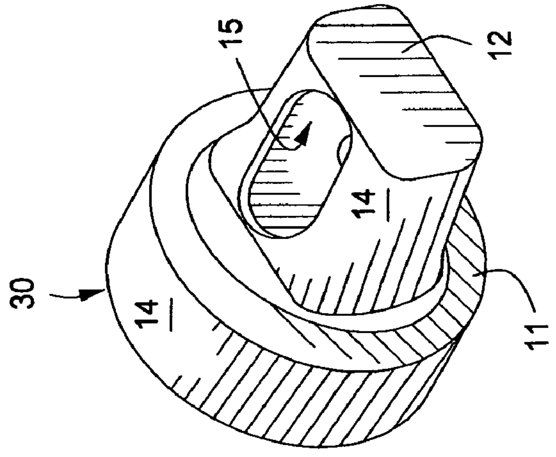
FIG. 6*b* is an isometric view illustrating one exemplary embodiment of a second portion of a base body.
Figure 6A:
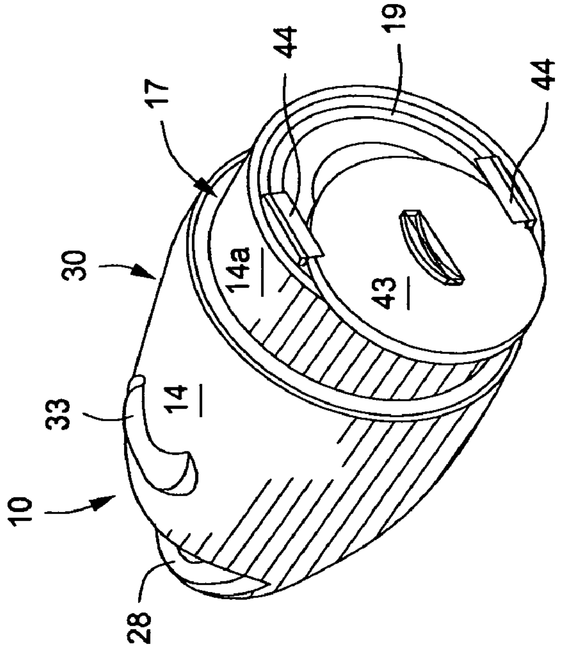
FIG. 6*a* shows an isometric view illustrating a power source stowed in a base body.

In one exemplary embodiment, the dial assembly 30 includes at least one alignment element 28. As shown in FIGS. 4*a* and 6*a*, the at least one alignment element 28 comprises a notch defined by the display body 6. In operation, the alignment element 28 is referenced tactilely, without the need for visual inspection of the illuminated display system 5, to enhance orientation toward the adjacent selector 33 for engaging the lighting operation sequence of the plurality of light emitters 22. Optionally, in one exemplary embodiment, the display body 6 defines a lens fastening interface 29 for receiving a fastening means of a type well known in the industry to secure the illuminated display system 5 to an injured user or object.

Specifically referring to FIG. 4*a*, in one exemplary embodiment, the base body 14 includes a first portion 11 and a second portion 12 extending outwardly from the first portion 11. FIGS. 7*b*-7*d* illustrate various embodiments for the second portion 12. In FIG. 7*b*, the second portion 12 comprises a resilient member for applying a compressive force against an in injured user. As shown, the embodiment of FIG. 7*b* includes a sensor assembly 57. Illustratively, the sensor assembly 57 includes an electrode 58 and an adhesive laminate 59 disposed on the resilient member and adjacent to the electrode 58 to facilitate continuous contact against the injured user. In one exemplary embodiment, the electrode 58 comprises a heart monitor. In FIG. 7*d*, the second portion 12 defines a storage chamber 56 for holding a variety of objects.

The storage chamber is configured to accommodate a wide range of useful items such as additional power sources such as batteries, electronic identification tags, radio frequency (RF) identification microprocessors, biomedical sensors like heart-rate sensors and other well known sensors, global positioning system (GPS) locators and other well known locators, memory storage devices, and emitters/receivers. Moreover, as shown in FIG. 7*d*, the second portion may define a fastening interface 15 for receiving a fastening means of a type well known in the industry to secure the illuminated display system 5 to an injured user or object.

In FIGS. 4*a*, 5*c*, and 7, the base body 14 defines a receiving chamber 19. The receiving chamber 19 is configured to accommodate a wide range of useful items such as power sources such as batteries, electronic identification tags, radio frequency (RF) identification microprocessors, biomedical sensors like heart-rate sensors and other well known sensors, global positioning system (GPS) locators and other well known locators, memory storage devices, and emitter/receivers. Operatively, in one exemplary embodiment, the receiving chamber 19 contains at least one battery for powering the interface module 40 including a desired light emitter from the plurality of light emitters 22. In one exemplary embodiment, the at least one battery comprises a lithium ion battery.

Figure 8F:
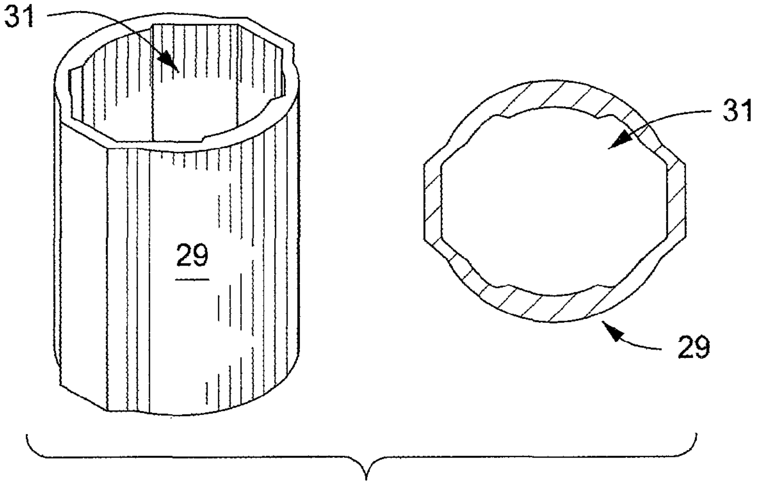
FIG. 8*f* illustrates a chamber support.

Shown in FIGS. 7*a* and 8*f*, a chamber support 29 is optionally disposed along the periphery of the receiving chamber 19 to structurally support the receiving chamber 19. Accordingly, the chamber support is composed of either a semi-rigid or rigid material. In operation, in one exemplary embodiment, the chamber support 29 comprises a tube having a support passageway 31 for receiving at least one battery therein while the outer surface of the chamber support 29 abuts along the periphery of the receiving chamber 19.

Referring to FIGS. 6*a*, 7*a, c*, 8*c*, and 9, at least one binder element 44 is provided for mechanically securing the power source to the interface module 40. The at least one binder element 44 is composed of either a semi-rigid or rigid material, such as an electrically conducive metal, metal alloy, or electrically conductive ceramic. Shown in FIGS. 8*c* and 9*a*, the at least one binder element 44 includes a module support 44*a* for coupling to the interface module 40 at one end and extends the length of the receiving chamber and thus power source therein, and includes a contact support holder 44*b* for coupling to a contact support 43 at another end. The at least one binder element 44 mechanically fastens the interface module 40 adjacent to the power source 62, such as among others a battery, and, in one illustration, electrically positions the battery's electrical terminals with the interface module 40 to supply power thereto. Electrically, in the illustration, the at least one binder element 44 establishes an electrical contact between the two electrical terminals of the at least one battery to complete a circuit for providing electrical power to the interface module 40. Those of ordinary skill in the art will readily recognize that, addition to the receiving chamber 19, the configuration of the at least one binder element 44, power source 62, and the contact support 43 may be reproduced within the storage chamber 56 of the second portion 12 to provide at least one additional power supply for powering the interface module 40.

Figure 9A:
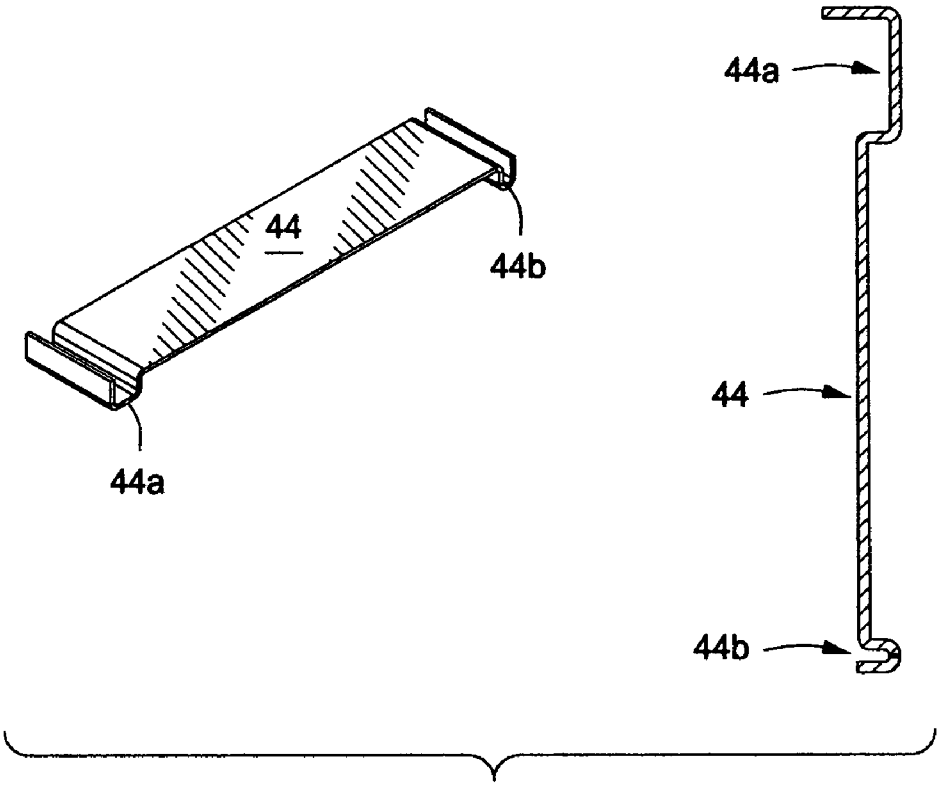
FIG. 9*a* illustrates a binder element for securing and electrically coupling the power source to the interface module.
Figure 9B:
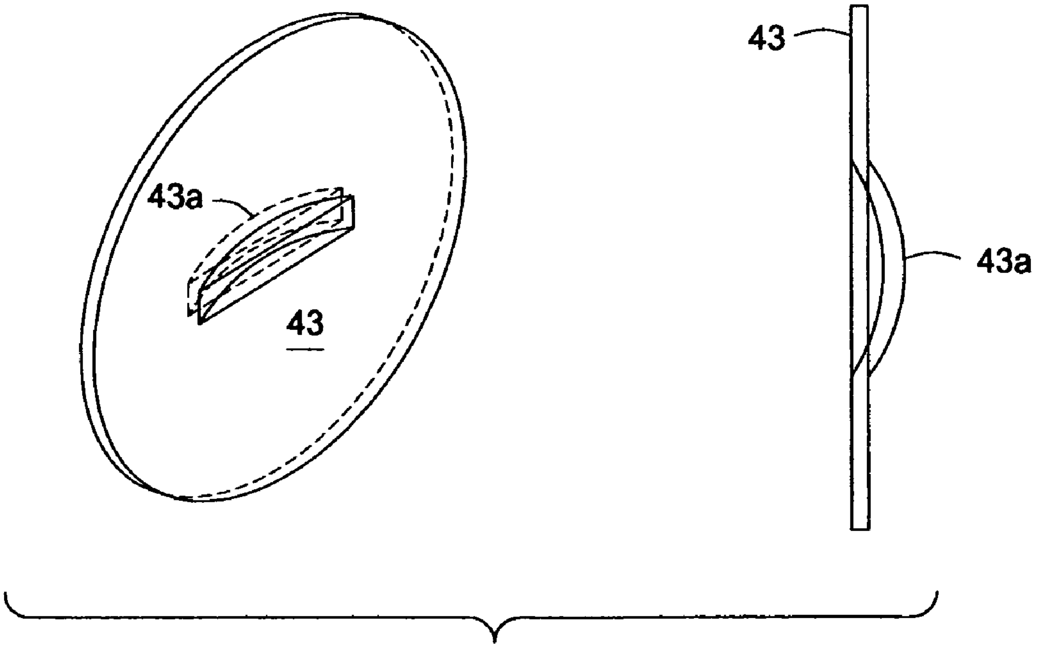
FIG. 9*b* shows a contact support for secured and electrical engagement with the power source and the binder element.

Moreover, as shown in FIGS. 6*a* and 9*b*, the contact support 43 is positioned against the electrical terminal of the battery 62 as the contact support 43 secured to the contact support holder 44*b*. In the illustration, the contact support 43 includes a resilient element 43*a* to dampen mechanical shock forces applied to the at least one battery 62 within the receiving chamber 19.

As shown in FIG. 6*a*, the contact support 43 is rendered to slide along or away from the contact support holder 44*b* to gain full access to the battery in the receiving chamber 19 so as to interchange an expended battery for a fully charged battery.

FIGS. 4*a* and 7*c*, illustrate an opening accessway 17. In one exemplary embodiment, the base body 14 defines the opening accessway 17. Operationally, in one exemplary embodiment, at least one portion of the illuminated display system 5 may be pulled apart from another portion of the illuminated display systems to gain access to the interface module 40, the receiving chamber 19, and the storage chamber 56 therein.

As illustrated in FIGS. 7*a* and *c*, in one exemplary embodiment, the base body 14 is configured to establish an interference fit at the opening accessway 17. Operatively, the base body 14 is pulled apart at the opening accessway 17 to expose the receiving chamber therein 19.

In particular, as shown in FIG. 7*a*, the base body 14 defines an attachment flange 14*a* at one end of the illuminated display system 5 so that the base body 14 of FIG. 7*c* is positioned over the attachment flange 14*a* to establish an interference fit. The base body 14 of FIG. 7*c* is pulled along the attachment flange 14*a* toward the interface module 40 to terminate at and thus define the opening accessway 17.

Referring to FIGS. 7 and 8, the illuminated display system 5 may further include an id tag processor 66. The id tag processor 66 may comprise a processor of a type well known in the industry such as a Radio Frequency Identification, RFID, processor.

As shown in FIGS. 8*b* and 8*c*, in one exemplary embodiment, the id tag processor 66 is coupled to the module processor 64, the memory unit 64*a*, and the power source 62. In one exemplary embodiment, as shown in FIG. 8*c*, the id tag processor 66 is coupled to an antenna array 49 for emitting and receiving signals in cooperation with the id tag processor 66. Illustratively, in one exemplary embodiment, the id tag processor 66 as coupled to the module processor 65, the memory unit 64*a*, and the power source 62 to collectively define an ultra high frequency active RFID tag. Optionally, as shown, the antenna array 49 is integral with a module substrate 21 of the interface module 40.

Those of ordinary skill in the art will readily recognize those configurations utilizing an id tag processor for facilitating identification signal emissions such as providing self-sustaining electronic identification tags for operative integration with the illuminated display system 5. In one exemplary embodiment, an id tag processor from a self-sustaining identification tag of a standard type well known in the industry integrates with a module processor from the illuminated display system to facilitate the generation of an identification signal as discussed below.

Figure 12:
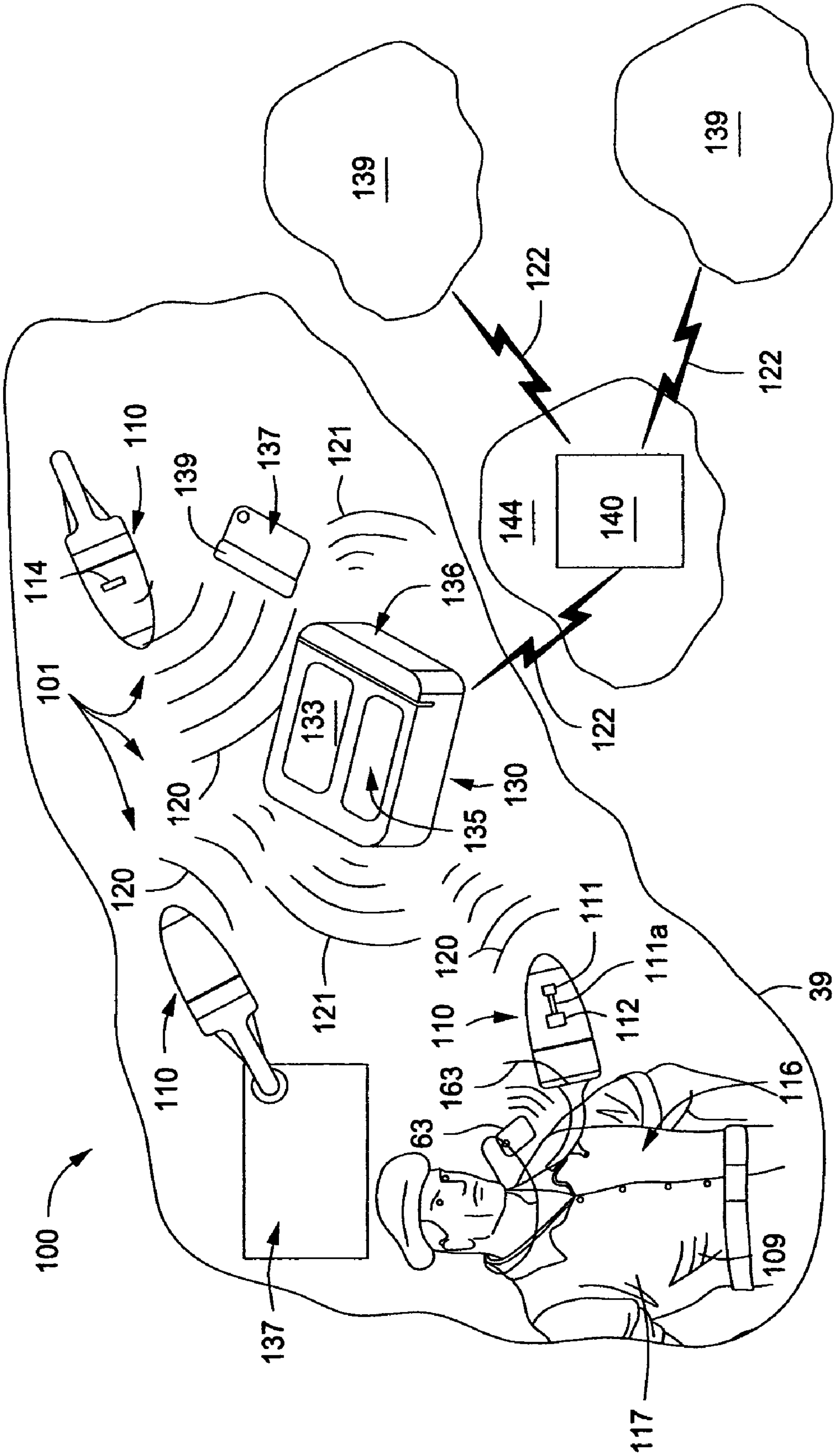
FIG. 12 is schematic diagram illustrating one exemplary embodiment of a networked triage system.

In one exemplary embodiment, as shown in FIG. 12, an id tag processor from an illuminated display system receives identifier information from an external source electronic identification tag such as a military radio frequency identification (RFID) or "dog" tag or electronic emissions from other sources such as from rescue or medical equipment. Accordingly, the id tag processor incorporates this information into a resulting identification signal for emission from the illuminated display system.

The id tag processor 66 generates an identification signal 120. In one exemplary embodiment, the identification signal 120 includes identifier information unique to the id tag processor 66. In one exemplary embodiment, the identification signal 120 includes personal information regarding the injured user associated with the illuminated display system 5. Illustratively, for example, personal information may include among others military dog tag information of: nationality, name, rank, serial number, religion, and detailed accounting of injury. The personal information is stored in the memory unit 64*a* and incorporated within the identification signal via either combination of the module processor 65 or the id tag processor 66.

In one exemplary embodiment, the id tag processor 66 and the module processor 65 cooperatively generate an identification signal. Accordingly, the identification signal includes identifier information and light emitter wavelength information. Illustratively, the identifier information includes, among other information, information unique to the particular id tag processor 66, information associated with the degree of injury, and personal information of the injured user.

In one exemplary embodiment, the identification signal includes last lit information regarding the illumination of a desired light emitter either before transmission from the illuminated display system 5 or on power loss of the illuminated display system 5. Accordingly, the degree of injury and triage status of the injured user is determined from the identification signal indicating the last active light emitter from the plurality of light emitters 22 of the illuminated display system 5.

Alternatively, in one exemplary embodiment as shown in FIGS. 7*d* and 8*a*, the illuminated display system 5 includes an electronic identification tag 63. In one exemplary embodiment, the electronic identification tag 63 is of a standard type well known in the industry such as, among others, an ultra high frequency active RFID tag, a battery assisted passive RFID tag and an ultra high frequency passive RFID tag.

Accordingly, the electronic identification tag 63 couples to the interface module 40 and generates an identification signal. In one exemplary embodiment, the electronic identification tag 63 is a self sustaining module that is provided by the networked triage system. The electronic identification tag 63 sends and receives identification signals associated with the illuminated display system 5.

Accordingly, the identification signal includes identifier information and light emitter wavelength information. Illustratively, the identifier information includes, among other information, information unique to the particular electronic identification tag 63, information associated with the degree of injury, and personal information of the injured user. In one exemplary embodiment, as discussed below, identifier information at least in part comes from an external source electronic identification tag hereinafter defined in this disclosure as an RFID tag that is not necessarily used for triage. Illustratively, examples of an external source identification tag include a military "dog" tag, a passport, a drivers license, and a credit card.

In one exemplary embodiment, the identification signal includes personal information regarding the injured user associated with the illuminated display system 5. Illustratively, for example, personal information may include among others military dog tag information of nationality; name; rank; serial number; religion; previous injuries; medical conditions as well as known allergic reactions; and detailed accounting of injury.

Referring to FIG. 12, a networked triage system 100 includes a plurality of illuminated display systems 101 and a portable network interface 130 coupled to the plurality of illuminated display systems 101. Generally, in one exemplary embodiment, the portable network interface 130 establishes an information hub for sending and receiving signals between the portable network interface 130 and the plurality of illuminated display systems 101.

Furthermore, the portable network interface 130 couples to a networked monitoring system 140 provided by the networked triage system 100 to send and receive network signals between the portable network interface 130 and the networked monitoring system 140. The networked monitoring system 140 couples to a plurality of portable network interfaces 130 and thus their respective plurality of illuminated display systems 101 to manage triage status within the broader network than a single user group having at least one portable network interface 130 and a plurality of illuminated display systems 101.

Illustratively, as shown in FIG. 12, the portable network interface 130 sends a network signal 122 to the networked monitoring system 140. In one exemplary embodiment, the network signal 122 includes at least in part an identification signal 120 corresponds with a particular illuminated display system 110 that is associated with an injured user 109. In response to the network signal 122 received from the portable network interface 130, triage providers associated with the networked monitoring system 140 provide instructions for the injured user by returning a network signal 122 to the portable network interface 130. Accordingly, the portable network interface 130 generates and sends a command signal 121 to the corresponding illuminated display system 110. In one exemplary embodiment, the command signal 121 generated by the portable network interface 130 is at least in part based on network signals 122 received by the portable network interface 130 from the network monitoring device 140. The illuminated display system 110 thus receives the command signal 121 and acts on the instructions provided therein such as, among other, light emitter illumination instructions, personal information updates, updates regarding injury, and updates regarding triage status.

It should be said that the networked triage system 100 as applied to medical triage is illustrative of one application for the system 100 out of many. Those of ordinary skill in the art will readily recognize situations other than medical triage that require electronic identification and illuminated status such as, among others, logistics, assets tracking and location, personnel awareness, inventory control, traffic control, safety, signaling, bundle dropping, perimeter marking, and maintenance.

In one exemplary embodiment, the portable network interface 130 establishes a local area network (LAN) or "user group" 139 for monitoring and assigning triage status to each injured user with a corresponding illuminated display system 110. Illustratively, the portable network interface 130 enables a relief provider such as a combat medic to compile and access information received from a plurality of illuminated display systems 101 where each illuminated display system 110 is coupled to an injured user such as a soldier near the portable network interface 130.

In one exemplary embodiment, the portable network interface 130 is coupled to a networked monitoring system 140 provided by the network triage system 100 to establish a wide area network (WAN) 144 for monitoring and assigning triage status to multiple groups of injured users each with a corresponding illuminated display system 110. Each user group 139 in the established wide area network 144 features at least one portable network interface 130 and a plurality of illuminated display systems 101 in operative engagement with the at least one portable network interface 130.

Illustratively, the network monitoring system 140 enables relief central command center such as a combat medical command center to compile and access information received from a plurality of user groups within the wide area network 144, where the plurality of user groups may constitute any group readily recognizable by those of ordinary skill in the art such as for example regional and operational groups for example, among others, a battlefield, a combat region, hurricane victims, a theater of war, within an entire branch of service and within the entire military. Each user group 139 includes a plurality of illuminated display systems 110 and at least one portable network interface 130.

As shown in FIG. 12, the networked triage system 100 includes a plurality of user groups and a networked monitoring system 140. Each user group 139 of the plurality of user groups communicates with the networked monitoring system 140 via network signals 122.

Each user group 139 includes a plurality of illuminated display systems 101 and a portable network interface 130. The portable network interface 130 is coupled to the plurality of illuminated display systems 101.

Similar to the above described, each illuminated display system couples to an injured user. Each illuminated display system 110 includes a plurality of light emitters. Each light emitter supplies a predetermined wavelength of light providing information relating to a corresponding predetermined status of the user. Each light emitter is selected from the plurality of light emitters according to a lighting operation sequence.

Each illuminated display system 110 further includes a dial assembly. The dial assembly includes an interface module and a selector coupled to the interface module.

The interface module includes a module processor 111, a memory unit 111*a*, and at least one programming interface coupled to the module processor 111. The memory unit 111*a* stores the lighting operation sequence.

Each illuminated display system 110 further includes an id tag processor 112. Accordingly, each illuminated display system emits an identification signal 120 via the id tag processor 112. Shown in FIG. 12, the portable network device 130 receives the identification signal 120.

In one exemplary embodiment, the id tag processor 112 is coupled to the module processor 111. The id tag processor 112 facilitates emission of an identification signal. Specifically, in one exemplary embodiment, the id tag processor 112 and the module processor 111 independently emit an identification signal 120 and a predetermined wavelength of light via a designated light emitter to, respectively, provide information relating to a corresponding predetermined status of the injured user. Moreover, the module processor 111 and the id tag processor 112 cooperatively work to generate the identification signal 120 to include both identifier information and light emitter wavelength information. In one exemplary embodiment, light emitter wavelength information includes information associated with which light emitter from the plurality of light emitters is illuminated to indicate the predetermined status of the user. As discussed below in FIG. 12, the identification signal 120 from the corresponding illuminated display system is then received by a portable interface device.

In one exemplary embodiment, the predetermined status of the user comprises medical triage status of a particular patient. In one exemplary embodiment, the predetermined status of the user comprises rescue and/or triage status of a particular patient.

Alternatively, in one exemplary embodiment, each illuminated display system 110 further includes an electronic identification tag 114 as described above. The electronic identification tag 114 includes an id tag processor.

Illustratively, in one exemplary embodiment shown in FIG. 12, an injured user 109 includes an electronic identification tag comprising a military dog tag 63 of a type well known in the industry. The military dog tag 63 emits an identification signal 163 including personal information associated with the injured user 109. The identification signal 163 is received by an id tag processor 112 of the illuminated display system 110 as shown in FIG. 12. Accordingly, a combat medic is able to position the illuminated display system 110 adjacent to a standard military issue dog tag 63 and retrieve information therefrom via the id tag processor 112. The personal information from the identification signal 163 is stored in a memory unit 111*a* coupled to the id tag processor 112. The personal information integrates with an identification signal 120 via the module processor 111 that is coupled to the memory unit 111*a*. In one exemplary embodiment, information regarding the status of the corresponding illuminated light emitter from the plurality of light emitters provided by the respective illuminated display system 110 stored in the memory unit 111*a* integrates with the identification signal 120 via the module processor 111. Optionally, as discussed in detail below, a sensor signal integrates within the identification signal 120 via a module processor 111 from an illuminated display system 110. The module processor 111 is coupled to the id tag processor 112, and a sensor assembly 116. Illustratively, the sensor assembly 116 is coupled to the injured user 109 to measure heart rate 117. Thus, ultimately, the identification signal 120 for the corresponding illuminated display system 110 is sent to a portable network interface 130 as shown in FIG. 12.

In one exemplary embodiment, the portable network interface 130 generates a network signal 122 based on the identification signal 120. In one exemplary embodiment, the network signal 122 includes information regarding the identification of each illuminated display system 110. In one exemplary embodiment, the network signal 122 includes information regarding the status of the corresponding illuminated light emitter from the plurality of light emitters provided by the respective illuminated display system 110. In one exemplary embodiment, the network signal 122 includes the identification signal 120.

Shown in FIG. 12, the portable network interface 130 generates a command signal 121 for receipt by a desired illuminated display system 110. Illustratively, the command signal 121 provides operational instructions to the desired illuminated display system 110 including, among others, to stop light emitter illumination, to start light emitter illumination, and to illuminate another light emitter. The command signal 121 includes illumination instructions for the illuminated display system 110 based on the corresponding identification signal for that desired illuminated display system 110.

In one exemplary embodiment, the portable network interface 130 generates a command signal 121 for receipt by a plurality of illuminated display systems 101. Illustratively, the command signal 121 provides operational instructions to the corresponding interface module of each illuminated display system 110 of the plurality of illuminated display systems 101 including, among others, to stop light emitter illumination, to start light emitter illumination, and to illuminate another light emitter.

In one exemplary embodiment, the portable network interface 130 generates a command signal 121 for receipt by each illuminated display system 110. Illustratively, the command signal 121 provides operational instructions to the corresponding interface module of each illuminated display system 110 including, among others, to stop light emitter illumination, to start light emitter illumination, and to illuminate another light emitter.

Referring to FIG. 12, the portable network interface 130 includes a manual interface 135 and a display 133 operatively coupled to the manual interface 135. In one exemplary embodiment, the manual interface 135 provides a status input for integration with a command signal 121 that is sent from the portable network interface 130 to the plurality of illuminated display systems 101. The status input at least in part incorporates with the corresponding triage status generated and stored by the portable network interface 130 as described below. Accordingly, the corresponding triage status is included at least in part to define a command signal emitted from the portable network interface 130 or used at least in part by at least one memory device 137.

In one exemplary embodiment, the manual interface 135 comprises a keypad having alphanumeric keys. In one exemplary embodiment, the manual interface 125 comprises an electronic input surface, such as, among others, a touch pad, a touch screen, an electronic tablet, and an electronic ink display. The display 133 indicates the triage status from each illuminated display system 110. Illustratively, in one exemplary embodiment, the display 133 indicates the status of an illuminated light emitter from a corresponding illuminated display system 110.

Illustrated in FIG. 12, the portable network interface 130 further includes at least one memory device 137 and an electronic interface 136. The electronic interface 136 is operatively coupled to the display 133 and to the manual interface 135. The electronic interface 136 communicates with the at least one memory device 137. Specifically, in one exemplary embodiment, the electronic interface 136 reads output and writes input electronically to the at least one memory device 137.

In one exemplary embodiment, the at least one memory device 137 stores identification signals 120 and command signals 121. In one exemplary embodiment, the at least one memory device 137 stores and provides triage status for a respective illuminated display system 110. The triage status includes, among other, last lit status provided by the respective illuminated display system 110 as well as detailed information regarding the injured user provided as a status input received by the portable network interface 130. The status input received by the portable network interface 130 is either entered directly from the manual interface 135 or provided within an identification signal 120 created at least in part by an id tag processor 112.

Accordingly, in one exemplary embodiment, the identification signal 120 includes identifier information and light emitter wavelength information. In one exemplary embodiment, the identification signal 120 includes information unique to an id tag processor within the respective illuminated display system 110 and includes personal information such as among others military dog tag information. Input received by the portable network interface 130 can be combined with identifier information from the identification signal 120 to define at least in part triage status. Illustratively, triage status collected by the portable network interface 130 for example includes the name of a soldier wearing the respective illuminated display system 110 is obtained from the identification signal 120. However, the specific injury, change in injury status, change in triage status, and name of the assessing medic or relief provider or any other missing information is provided by a direct input to the portable network interface 130 such as, among others, input received from the manual interface 135, the electronic interface 136, in memory from the portable network interface 130, and network signals 122 from the networked monitoring system 140.

In one exemplary embodiment, the triage status collected by the portable network interface 130 including at least in part personal information, injury information, and triage information is updated continuously with the portable network interface 130. The portable network interface 130 sends command signals 121 to synchronize the updated triage status with the corresponding illuminated display system 110. In effect, the triage status of the injured user is continuously updated with the portable network interface 130 and saved in the memory unit 111 of the respective illuminated display system 110 as the injured user 109 is brought from the field, along a designated rescue evacuation route, and to a final destination for receiving care. Accordingly, at the final destination for receiving care, the illuminated display system 110 accurately reflects the current status of the injured user 109 as the updated triage status is stored in memory 111, accessed via the module processor 111, and sent from the illuminated display system 110 as an identification signal 120 and as displayed by a corresponding illuminated light emitter to the final destination for receiving care.

In one exemplary embodiment, the at least one memory device 137 stores and provides triage status for at least one illuminated display system 110. The triage status from the memory device 137 integrates with a command signal 121.

In one exemplary embodiment, each memory device 137 is color coded. Illustratively, in one exemplary embodiment, each memory device 137 is color coded based on a color scheme associated with medical triage. Optionally, each memory device 137 includes indicia. In one exemplary embodiment, each memory device 137 includes indicia based on a predetermined scheme associated with medical triage.

Operatively, one exemplary method for organizing medical care may be appreciated as follows. A plurality of illuminated display systems 101 is provided such that each illuminated display system 110 includes an identification or "id" tag processor 112. An illuminated display system 110 from the plurality of illuminated display systems 101 is coupled to an injured user. The identification tag processor 112 facilitates the generation and emission of an identification signal 120.

The illuminated display system 110 includes a plurality of light emitters. Each light emitter supplies a predetermined wavelength of light than the other light emitters from the plurality of light emitters 101. Each respective predetermined wavelength provides information relating to the corresponding predetermined status of the user.

A portable network interface 130 receives at least one identification signal 120 from the illuminated display system 110. Moreover, the portable network interface 130 receives a plurality of identification signals from corresponding illuminated display systems 110 of the plurality of illuminated display systems 101. In one exemplary embodiment, each identification signal 120 from a respective illuminated display system 110 of the plurality of illuminated display systems 101 is received by the portable network interface 130. Furthermore, the portable network interface 130 includes a manual interface, an electronic interface, and a display operatively coupled to the manual interface and the electronic interface.

A predetermined color is assigned to each memory device 137 of a plurality of memory devices. A clinical assessment is administered to the injured user and thus a triage status is assigned to the injured user based on a pre-determined degree of injury.

A memory device 137 is selected having a color consistent with the triage status of the injured user. The memory device

137 is coupled to the electronic interface 136. Specifically, in one exemplary embodiment, the electronic interface 136 reads input and writes output electronically to the at least one memory device 137. Illustratively, in one exemplary embodiment, input includes command signals, triage status, identification signals, and other information received from at least one illuminated display system 110 and the manual interface 135. In one exemplary embodiment, output to the memory device 137 includes command signals, triage status, identification signals, and other information received from at least one illuminated display system 110 and the manual interface 135. In one exemplary embodiment, the selected memory device 137 is assigned and either coupled to the injured user or used as a reference by triage providers.

In one exemplary embodiment, a desired light emitter from the illuminated display system 110 is selected based on the triage status for illumination thereof. After loss of power to the plurality of light emitters 101, the desired light emitter is re-illuminated based on the triage status. In one exemplary embodiment, the portable network interface 130 sends command signals to the plurality of light emitters 101 to re-illuminated the desired light emitter.

The at least one memory device 137 is used in medical triage in conjunction with the desired illuminated display system. Collectively, the memory devices 137 are used by triage providers as a cross reference indicating the triage status of many injured users that were assessed and received a corresponding illuminated display system 110. In one exemplary embodiment, the at least one memory device 137 comprises a memory card that is color coded based on a color scheme associated with medical triage. Illustratively, in one exemplary embodiment, a combat medic is able to collect a plurality of memory devices 137 from many triage locations and remotely access triage and relief priorities in a field clinic in the particular situation where wireless communications over distances is either tenuous or non-existent. In one exemplary embodiment, the memory device 137 is attached to an injured user in situations of good visibility or in the event of an inoperable, corresponding illuminated display system.

A sensor signal integrates within an identification signal via a module processor 111 from an illuminated display system 110. The module processor 111 is coupled to a corresponding identification tag processor 112, and a sensor assembly 116. The portable network interface 130 reads the identification signal generated by the illuminated display system 110 that includes the sensor signal. Accordingly, the portable network interface 130 emits a control signal to the illuminated display system 110 to select another light emitter for illumination based on the sensor signal received by the portable network interface 130.

Illustratively, a sensor assembly 116 that is integral with an illuminated display system 110 is placed close to a soldier's heart to monitor heart rate. A sensor signal emitted by the sensor assembly 116 once indicating that the soldier is in critical condition changes to indicate the soldier is dead. A resulting identification signal 120 is received by the portable network interface 130 and a command signal 121 is then sent from the portable network interface 130 to the corresponding illuminated display system 110. The command signal 121 indicates to the module processor 111 to select another light emitter for illumination, such as a light emitter that provides a blue wavelength band of visible light indicating the soldier is dead according to a triage color scheme well known in the industry.

Although the present invention has been described in detail, it should be understood that various changes, substitutions, and alterations could be made hereto without departing from the spirit and scope of the invention as defined by the appended claims.

I claim:

1. A networked triage system comprising:
a plurality of user groups,
each user group including
a plurality of illuminated display systems,
each illuminated display system couples to an injured user and includes
a plurality of light emitters,
each light emitter providing a predetermined wavelength of light than the other light emitters from the plurality of light emitters,
each respective predetermined wavelength providing information relating to a corresponding predetermined status of the user, and
an id tag processor,
the id tag processor facilitates emission of an identification signal, and
a portable network interface coupled to the plurality of illuminated display system, the portable network interface receiving the identification signal; and
a networked monitoring system,
each user group of the plurality of user groups in communication with the networked monitoring system.

2. The networked triage system according to claim 1 wherein the portable network interface generates a command signal for receipt by a desired illuminated display system in the network triage system, the command signal including illumination instructions for the illuminated display system.

3. The networked triage system according to claim 2 wherein each user group communicates with the networked monitoring system with network signals, and wherein the portable network interface generates a network signal based on the identification signal, the network signal including information regarding the identification of each illuminated display system and the status of the corresponding illuminated light emitter from each illuminated display system.

4. The networked triage system according to claim 3 wherein the command signal generated by the portable network interface is at least in part based on network signals received by the portable network interface from the networked monitoring system.

5. The networked triage system according to claim 1 the portable network interface including a manual interface and a display coupled to the manual interface, the display indicating the triage status from an illuminated display system.

6. The networked triage system according to claim 1 wherein at least one memory device stores triage information.

7. The networked triage system according to claim 6 wherein the at least one memory device is used in medical triage in conjunction with a desired illuminated display system, and stores identification signals and command signals associated with the desired illuminated display system.

8. The networked triage system according to claim 6 wherein the at least one memory device is color coded based on a color scheme associated with medical triage.

9. A method for organizing medical care comprising the steps of:
providing a plurality illuminated display systems, each illuminated display system including an identification tag processor;
administering a clinical assessment of an injured user and assigning a triage status to the injured user based on a pre-determined degree of injury;

coupling an illuminated display system from the plurality of illuminated display systems to an injured user and generating an identification signal with the identification tag processor; and receiving the identification signal with the portable network interface, the portable network interface receiving a plurality of identification signals, each identification signal from a respective illuminated display system of the plurality of illuminated display systems.

10. The method for organizing medical care according to claim 9 further including the steps of:

generating a command signal with the portable network interface, the command signal at least in part defined by the triage status; and sending the command signal from the portable network interface to the respective illuminated display system.

11. The method for organizing medical care according to claim 10 further comprising the step of selecting a desired light emitter from the respective illuminated display system for illumination based on the command signal.

12. The method for organizing medical care according to claim 9 further comprising the steps of:

assigning a predetermined color to each memory device of a plurality of memory devices;

selecting a memory device having a color consistent with the triage status of the injured user; and coupling the selected memory device to the portable network interface.

13. The method for organizing medical care according to claim 9 further comprising the steps of:

integrating a sensor signal within an identification signal with a module processor from an illuminated display system, the module processor coupled to the corresponding identification tag processor and a sensor assembly;

reading the identification signal with the portable network interface; and emitting a command signal from the portable network interface to the respective illuminated display system to select another light emitter for illumination from the illuminated display system.

14. An illuminated display system comprising:

a base assembly, a display interface coupled to the base assembly, the display interface including a plurality of light emitters, each light emitter providing a predetermined wavelength of light than the other light emitters from the plurality of light emitters, each respective predetermined wavelength providing information relating to a corresponding predetermined status of the user, each light emitter is selected from the plurality of light emitters according to a lighting operation sequence; and a dial assembly, the dial assembly including an interface module and selector coupled to the interface module, the interface module including a module processor and a memory unit, the memory unit storing the lighting operation sequence, and the module processor receives the voltage from the selector indicating the desired light emitter for illumination based on the lighting operation sequence.

15. The illuminated display system according to claim 14 further comprising an id tag processor coupled to the module processor, and wherein the id tag processor and the module processor cooperatively generate an identification signal, the identification signal including identifier information and light emitter wavelength information.

16. The illuminated display system according to claim 15 further comprising an electronic identification tag coupled to the interface module, the electronic identification tag supplying personal information to the module processor, the id tag processor facilitating emission of an identification signal based on the identifier information.

17. The illuminated display system according to claim 14 further comprising at least one programming interface coupled to the module processor, and wherein the at least one programming interface receives a command sequence, the command sequence integrates with the lighting operation sequence to define a reprogrammed lighting operation sequence, each light emitter is selected from the plurality of light emitters according to the reprogrammed lighting operation sequence.

18. The illuminated display system according to claim 17 wherein the reprogrammed lighting operation sequence is stored in memory via the module processor.

19. The illuminated display system according to claim 15 wherein the identification signal includes last lit information.

20. The illuminated display system according to claim 19 wherein, on reestablishment of power to the interface module, the module processor retrieves the last lit information from the memory unit to illuminate the desired light emitter.

* * * * *